United States Patent
Urella et al.

[11] Patent Number: 5,911,314
[45] Date of Patent: Jun. 15, 1999

[54] HEADSET EAR SEAL

[75] Inventors: Richard M. Urella, Charlton; Robert E. Dalbec, Paxton; Louis J. Kiwak, Webster, all of Mass.

[73] Assignee: David Clark Company Inc., Worcester, Mass.

[21] Appl. No.: 09/052,243

[22] Filed: Mar. 31, 1998

[51] Int. Cl.⁶ .............................. A42B 1/06; G10K 11/00
[52] U.S. Cl. ...................... 2/209; 2/410; 2/414; 2/423; 381/372
[58] Field of Search ............................. 2/209, 171, 208, 2/410, 411, 412, 414, 423; 381/371, 372, 373–380, 370

[56] References Cited

U.S. PATENT DOCUMENTS

| | | |
|---|---|---|
| D. 246,242 | 11/1977 | Bellini . |
| D. 254,183 | 2/1980 | Doodson . |
| D. 302,429 | 7/1989 | Leer . |
| 2,191,055 | 2/1940 | Wensky . |
| 2,235,372 | 3/1941 | Kalbitz . |
| 2,408,494 | 10/1946 | Veneklasen . |
| 2,989,598 | 6/1961 | Touger et al. . |
| 2,990,553 | 7/1961 | Ulrich et al. . |
| 3,030,458 | 4/1962 | Gongoll . |
| 3,051,961 | 9/1962 | Clark . |
| 3,052,887 | 9/1962 | Sockel et al. . |
| 3,073,410 | 1/1963 | Gongoll et al. . |
| 3,220,505 | 11/1965 | Hargrave . |
| 3,408,658 | 11/1968 | Beguin et al. . |
| 3,457,565 | 7/1969 | Simpson et al. . |
| 3,571,813 | 3/1971 | Allen . |
| 3,593,341 | 7/1971 | Aileo . |
| 3,686,691 | 8/1972 | Anderson . |
| 3,796,855 | 3/1974 | Brown et al. . |
| 3,862,451 | 1/1975 | Miller et al. . |
| 4,071,717 | 1/1978 | Fidi et al. . |
| 4,087,653 | 5/1978 | Frieder, Jr. et al. . |
| 4,139,743 | 2/1979 | Flygstad . |
| 4,156,118 | 5/1979 | Hargrave . |
| 4,160,135 | 7/1979 | Görike . |
| 4,302,635 | 11/1981 | Jacobsen et al. . |
| 4,389,542 | 6/1983 | Gorike ..................................... 179/1 R |
| 4,472,607 | 9/1984 | Houng . |
| 4,499,593 | 2/1985 | Antle . |
| 4,588,868 | 5/1986 | Bertagna et al. . |
| 4,674,134 | 6/1987 | Lundin . |
| 4,771,454 | 9/1988 | Wilcox, Jr. . |
| 4,856,118 | 8/1989 | Sapiejewski . |
| 4,944,361 | 7/1990 | Lindgren et al. . |
| 4,958,697 | 9/1990 | Moody . |
| 4,987,592 | 1/1991 | Flagg . |
| 5,003,631 | 4/1991 | Richardson . |
| 5,018,599 | 5/1991 | Dohi et al. . |
| 5,020,163 | 6/1991 | Aileo et al. . |
| 5,023,955 | 6/1991 | Murphy, II et al. . |
| 5,068,923 | 12/1991 | Sjoqvist ..................................... 2/209 |
| 5,117,464 | 5/1992 | Jones et al. . |
| 5,138,722 | 8/1992 | Urella et al. . |
| 5,185,807 | 2/1993 | Bergin et al. . |
| 5,241,971 | 9/1993 | Lundin . |
| 5,293,647 | 3/1994 | Mirmilshteyn et al. . |

*Primary Examiner*—John J. Calvert
*Assistant Examiner*—Tejash P. Patel
*Attorney, Agent, or Firm*—Samuels, Gauthier & Stevens

[57] ABSTRACT

An earcup assembly is disclosed for use in a headset. The earcup assembly includes an earseal ring that includes an outer peripheral surface, an inner peripheral surface that provides an opening an annular base surface for securing the earseal to the headset, and an annular exposed surface opposite the base surface. The inner surface includes a first portion adjacent the exposed surface that provides a first peripheral distance around the opening and the inner surface further includes a second portion adjacent the base surface that provides a second peripheral distance around the opening. The second distance is larger than the first distance.

17 Claims, 3 Drawing Sheets

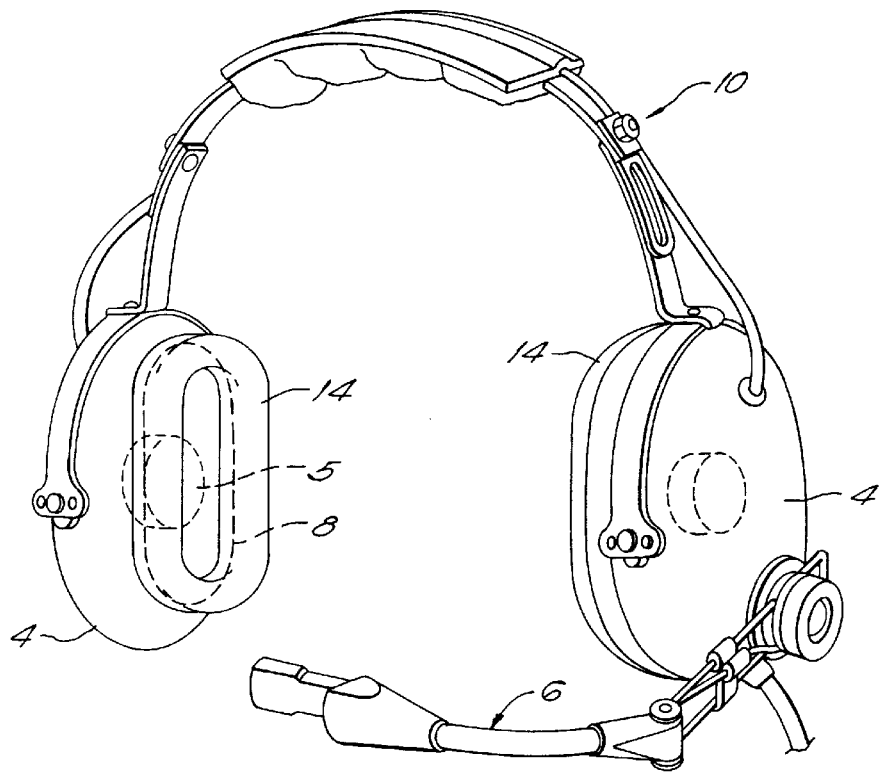
FIG. 1
(PRIOR ART)
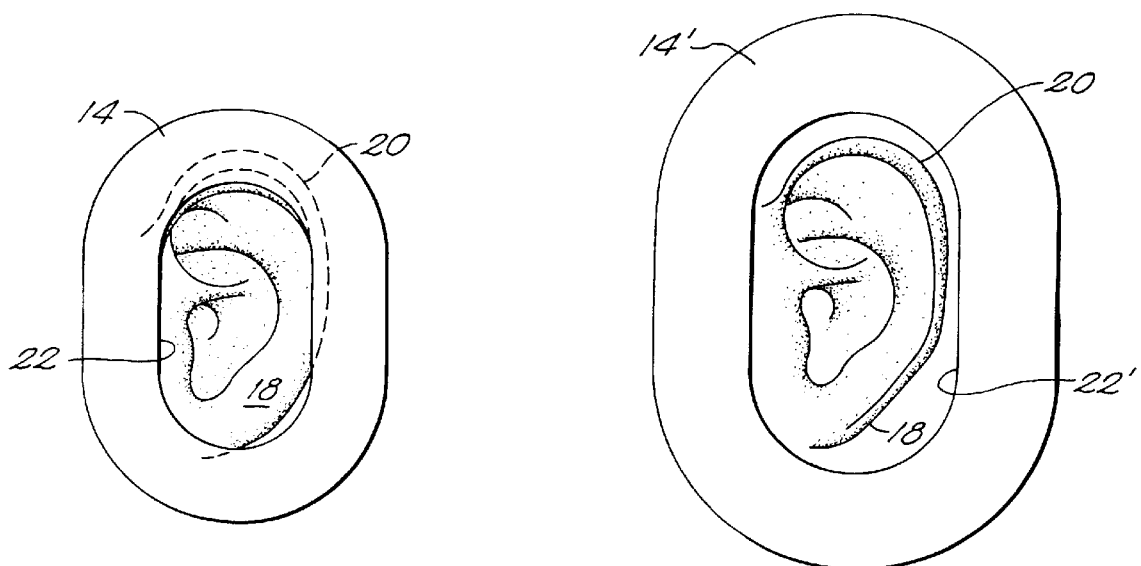
FIG. 2
(PRIOR ART)
FIG. 3

HEADSET EAR SEAL

BACKGROUND OF THE INVENTION

The invention relates to circumaural headsets having ear domes adapted to attenuate noise. Such headsets include communication equipment as well as ear protectors and other like noise attenuating devices.

Circumaural hearing protectors function by enclosing the ears of a user within earcups, typically plastic domes. Comfortable ear seals are interposed between the earcups and the user's head to assist in isolating the ears from offending noise originating outside the earcups. The earcups are typically attached to a spring and suspension assembly that applies a force urging the ear seals in place against the head of a user. Proper adjustment of the headband clamping force is critical to achieving optimum comfort and noise attenuation levels. Excessive force can cause discomfort, whereas insufficient force can result in an inadequate earcup seal allowing ambient noise to enter into the ear dome cavity. The difficulty in providing improved noise attenuation without detracting from comfort has been long recognized. See for example, U.S. Pat. Nos. 5,923,647; 5,590,213; 5,185,807, 5,138,722; 5,020,163; 4,944,361; 4,856,118; 4,674,134; 3,593,341; 3,571,813; and 2,408,494.

Ear seals are typically designed to accommodate a wide range of users having differently sized heads and ears. Users with particularly large ears, however, suffer certain difficulties. Such a user may either fold back the helix of his or her ear causing discomfort, or may place the ear seal against the helix of his or her ear, pressing the ear against the head. The presence of a portion of the user's ear between the ear seal and the user's head, significantly detracts from the noise attenuation capabilities of the headset. Moreover, such users are generally under some discomfort at normal ear seal pressure since the ear seal presses against the helix of the user's oversized ear. Such a user may decrease the pressure against their head, thereby providing more comfort but a loss in noise attenuation. Or the user may increase the pressure of the ear seals against their head in an effort to improve noise attenuation, thereby causing greater discomfort.

There is a need, therefore, for an earseal for a noise attenuating headset, that provides maximum comfort and noise attenuation for users with oversized ears.

SUMMARY OF THE INVENTION

The invention provides an earcup assembly for use in a headset. The earcup assembly includes an earseal ring that includes an outer peripheral surface, an inner peripheral surface that provides an opening, an annular base surface for securing the earseal to the headset, and an annular exposed surface opposite the base surface. The inner surface includes a first portion adjacent the exposed surface that provides a first peripheral distance around the opening. The inner surface further includes a second portion adjacent the base surface that provides a second peripheral distance around the opening, such that the second distance is larger than the first distance.

In an embodiment of the inventions the earseal ring includes a step portion on the inner peripheral surfaces and in further embodiments the earseal ring further includes a step portion on the outer peripheral surface.

BRIEF DESCRIPTION OF THE DRAWINGS

The following detailed description of the illustrated embodiments may be further understood with reference to the accompanying drawings in which:

FIG. 1 is a perspective view of a headset including ear seals of the prior art;

FIG. 2 is a top plan view of an earseal of FIG. 1 placed above an oversized ear;

FIG. 3 is a top plan view of an oversized earseal placed above an oversized ear;

Figure 4:
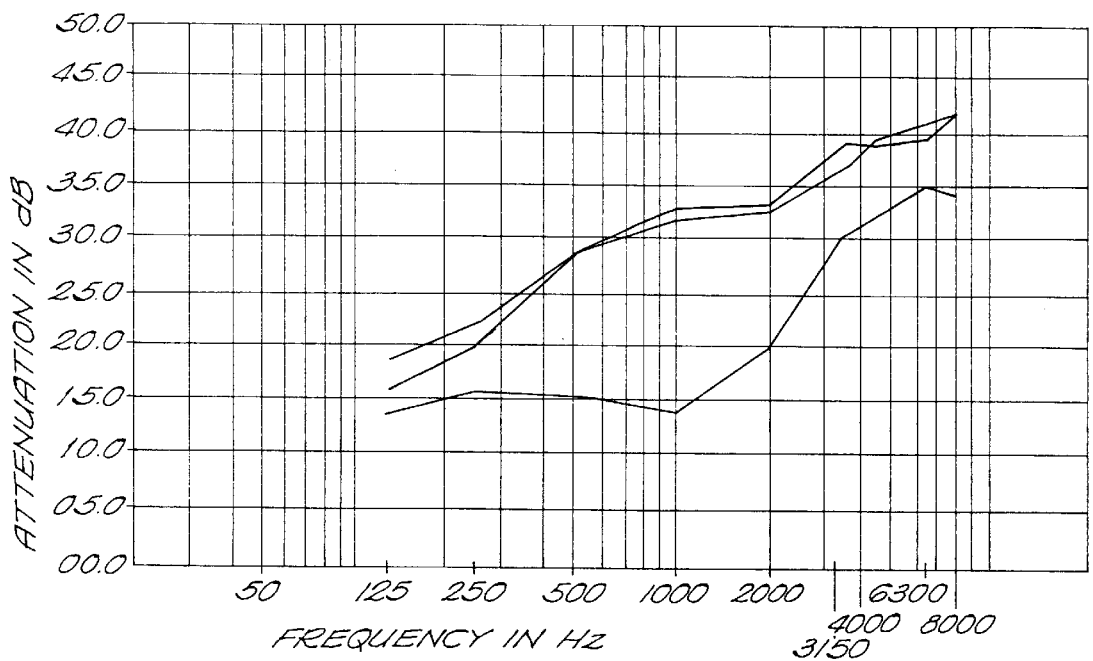
FIG. 4 is graph comparing noise attenuation of various earseals.

The drawings are not necessarily to scale and are shown for illustrative purposes only.

DETAILED DESCRIPTION OF THE ILLUSTRATED EMBODIMENTS

A conventional headset 10 is shown in FIG. 1 and includes a pair of earcups 4, each of which includes an earseal 14 generally made from a soft compliant material, attached to a plastic dome. The earseals may be attached to lip portions 8 on the domes by any known method such as the method disclosed in U.S. Pat. No. 5,138,722, the disclosure of which is hereby incorporated by reference. In other embodiments, the earseals may be attached to the earcups by bonding the earseals to retainer rings that snap engage onto the plastic domes as disclosed in U.S. Pat. No. 5,590,213, the disclosure of which is hereby incorporated by reference. The headset may further be a communication device including a speaker 5 and a microphone boom assembly 6.

The earseals may include any dilatant, foam, or other material, such as a mixture of a dilatant silicone compound and a silicone oil, surrounded by a urethane sheath as disclosed in U.S. Pat. No. 5,138,722. The earseal may also include a ring of soft compliant material such as a dielectric silicone gel disposed within the earseal together with a dilatant material. The headband assembly may be any known type such as, for example, those disclosed in U.S. Pat. Nos. 5,138,722 and 5,590,213.

As shown in FIG. 2, conventional earseals are too small for persons having an oversized ear 18. Specifically, the helix 20 of the oversized ear 18 will be trapped beneath the earseal 14, and not fully exposed in the opening 22 as intended. As shown in FIG. 3, the size of the earseal 14' may simply be increased to accommodate the oversized ear 18 within the opening 22'.

Such an oversized earseal, however, has been found to yield poor performance in noise attenuation. Noise attenuation may be measured for a conventional earseal and an oversized earseal as follows. The conventional earseal has inner dimensions of 1.5 inches wide by 2.5 inches tall, and outer dimensions of 3.0 inches wide by 4.0 inches tall. Such an earseal has a surface area that contacts a user's head of 6.80 sq. inches. The oversized earseal has inner dimensions of 2.0 inches wide and 3.0 inches tall, and outer dimensions of 3.75 inches wide and 4.75 inches tall. The surface area of the oversized earseal that contacts a user's head is 9.65 sq. inches. In accordance with ANSI S3.19-1974, test were performed on ten subjects, with three tests per subject at each frequency. The headband force with the conventional earseal is 2.1 lbs, and the headband force with the oversized earseal is 2.0 lbs. The results of the test are shown in Table 1.

TABLE 1

| Earseal | 125 Hz | 250 Hz | 500 Hz | 1000 Hz | 2000 Hz | 3150 Hz | 4000 Hz | 6300 Hz | 8000 Hz |
|---|---|---|---|---|---|---|---|---|---|
| Conventional | | | | | | | | | |
| Mean | 18.7 | 22.2 | 28.7 | 32.0 | 32.8 | 36.2 | 38.0 | 40.2 | 41.2 |
| Standard Deviation | 3.5 | 2.7 | 2.9 | 2.1 | 1.7 | 3.7 | 3.8 | 3.6 | 4.5 |
| Oversized | | | | | | | | | |
| Mean | 14.0 | 15.4 | 15.2 | 14.3 | 19.9 | 30.0 | 34.9 | 35.1 | 34.2 |
| Standard Deviation | 2.5 | 2.6 | 1.7 | 1.9 | 2.7 | 3.2 | 3.8 | 2.7 | 3.6 |

These above means are shown in the graph in FIG. 4. The means for the conventional earseal are represented by the line indicated at A, and the means for the oversized earseal are represented by the line indicated at B.

For the conventional earseal the Noise Reduction Ratio (NRR) is 24 dB, and for the oversized earseal the NRR is only 12 dB. Simply increasing the size of the earseal increases the peripheral area exposed to noise, and requires that the earseal adapt to greater changes in the surface area where it contacts the user's head.

It has been discovered, that although increasing the outer peripheral area of the earseal decreases performance, and although decreasing the uniform thickness of the earseal decreases noise attenuation performance, earseals may be designed that accommodate oversized ears, yet provide noise attenuation performance comparable with that of conventional earseals. It has further been discovered that only the portion of the earseal that is adjacent the user's head should have a minimum inner diameter.

Figure 5:
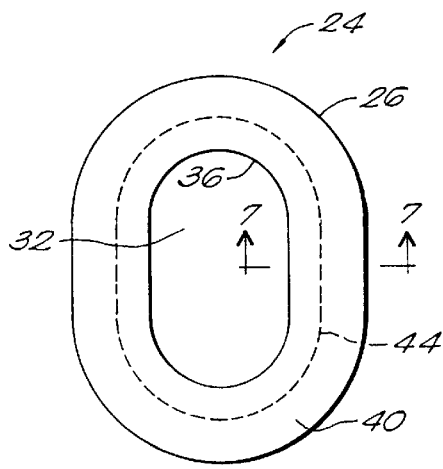
FIG. 5 is a top plan view of an earseal of the invention.
Figure 6:
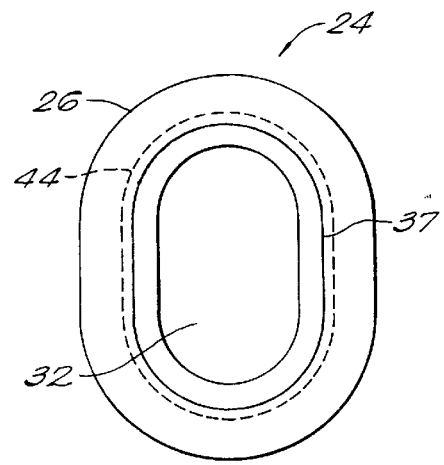
FIG. 6 is a bottom view of the earseal of FIG. 5.
Figure 7:
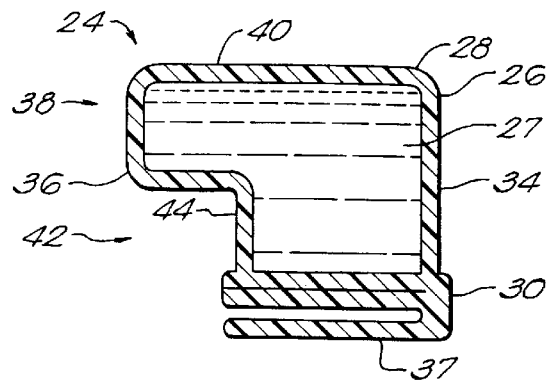
FIG. 7 is a sectional view of the earseal of FIG. 5 taken along line 7—7 thereof.

FIGS. 5 and 6 show top and bottom views respectively of an earseal 24 of the invention that is adapted to be worn by a user with oversized ears, and provides sufficient attenuation. The earseal 24 includes a thin flexible ring shaped sheath 26 having an upper portion 28 and a base portion 30. The sheath 26 is typically formed from polyurethane or the like, and surrounds an opening 32 for receiving an ear of a user. The bottom surface of the base portion 30 may be adhered to a conventional earseal retainer by adhesive, or may include an annular flap 37 as shown in FIG. 7 for engaging the annular lip 8 on the dome shown in phantom in FIG. 1 as further disclosed in U.S. Pat. No. 5,138,722.

The noise attenuating material within the sheath 26 may be any conventional material such as a mixture of a dilatent silicone compound and a silicone oil. An inner sheath of a thin flexible material may also be provided to enclose the ring of noise attenuating material 27, and the earseal may further include a ring of soft compliant material such as a dielectric gel also disposed within the sheath 26 in accordance with U.S. Pat. No. 5,138,722.

As shown in FIG. 7, the earseal 24 includes an outer peripheral surface 34 and an inner surface 36. The inner surface 36 includes a first portion 38 adjacent the surface 40 that contacts the user's head. The inner surface 36 also includes a second portion 42 that is adapted to accommodate an oversized ear. The second portion 42 includes a surface 44 that has a larger inner dimension than that of the surface of the first portion 38.

EXAMPLE 1

In one embodiment of the invention, an earseal of the invention has a first set of inner dimensions of 1.5 inches in width and 2.5 inches in length for the first portion 38 adjacent the user's head. The earseal has a second set of inner dimensions of 2.0 inches in width and 3.0 inches in length for the second portion 42. The outer dimensions are 3.25 inches in width and 4.25 inches in length. The surface area of the earseal that contacts the user's head is 8.27 inches. The same tests were done as above in accordance with ANSI S3.19-1974 on a headset including earseals of the invention. The headband force was 2.1 lbs. The results of the tests are shown in Table 2.

TABLE 2

| Earseal of Example 1 | 125 Hz | 250 Hz | 500 Hz | 1000 Hz | 2000 Hz | 3150 Hz | 4000 Hz | 6300 Hz | 8000 Hz |
|---|---|---|---|---|---|---|---|---|---|
| Mean | 15.5 | 19.9 | 28.6 | 33.3 | 33.2 | 38.8 | 38.1 | 39.2 | 41.2 |
| Standard Deviation | 3.2 | 2.5 | 2.7 | 2.1 | 2.4 | 3.7 | 3.2 | 4.4 | 4.1 |

The earseal of Example 1 provides an NRR of 23 dB which is comparable to that of the conventional earseal. The earseal provides a 21.6% increase in surface area to disburse the headband clamping force, resulting in a 17.8% reduction in the clamping force psi. Although the earseal provides a 57% larger opening for the ear (as provided by the second portion 42), the noise attenuation performance of the earseal is comparable to that of the conventional earseal. The graph in FIG. 4 shows the mean values for the various frequencies above as indicated at C. These values favorably compare with those of the conventional earseal.

Figure 8:
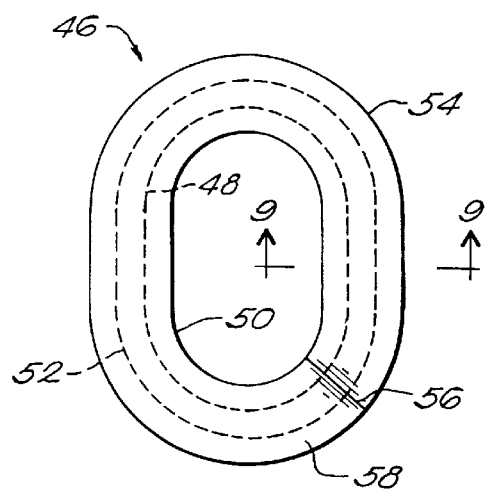
FIG. 8 is a top plan view of another earseal of the invention.
Figure 9:
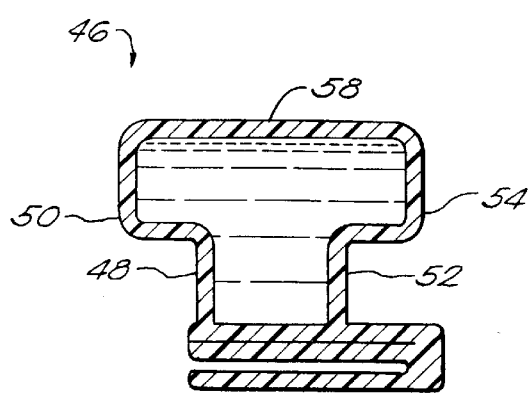
FIG. 9 is a sectional view of the earseal of FIG. 8 taken along line 9—9 thereof.

As shown in FIGS. 8 and 9, in another embodiment of the invention (Example 2), another earseal 46 of the invention may further include not only an inset surface 48 on its inner surface 50, but also an inset surface 52 on its outer surface 54 as shown. The remaining elements of the earseal 46 may be similar to those discussed above with reference to FIGS. 5 through 7. The earseal 46 permits the use of less dilatent material while still obtaining satisfactory noise attenuation. The earseal 46 of FIGS. 8 and 9 may further include a raised portion 56 on its exposed surface 58 to accommodate the depression in a person's head between the jaw and the neck.

Those skilled in the art will appreciate that modifications and variations may be made to the above disclosed embodiments without departing from the spirit and scope of the invention.

What is claimed is:

1. An earseal for use in a headset and adapted to accommodate a helix of a user's ear, said earseal comprising:

an annular base providing a distal surface extending between inner and outer peripheral edges of said annular base, said distal surface being adapted for securing said earseal to the headset;

an annular top providing a proximal surface extending between inner and outer peripheral edges of said annular top, said proximal surface being adapted for contacting a user's head;

an outer peripheral surface in communication with both said outer peripheral edge of said annular base and said outer peripheral edge of said annular top; and an inner peripheral surface in communication with both said inner peripheral edge of said annular base and said inner peripheral edge of said annular top, said inner peripheral surface providing a helix accommodating recess that is adapted to accommodate the helix of a user's ear, said helix accommodating recess extending toward said outer peripheral surface of said earseal a distance of at least about 20 percent of the distance between said inner and outer peripheral edges of said annular top.

2. An earcup assembly as claimed in claim 1 wherein said proximal surface has an area of less than about 9 square inches.

3. An earcup assembly as claimed in claim 1, wherein said earcup assembly provides attenuation of at least about 20 decibels for signals between about 1000 Hz and 2000 Hz.

4. An earcup assembly as claimed in claim 1, wherein said helix accommodating recess defines a first portion of said inner peripheral surface that is adjacent said proximal surface, and a second portion of said inner peripheral surface that is adjacent said distal surface, said first portion comprising at least 20 percent of a distance between said proximal and distal surfaces.

5. An earcup assembly as claimed in claim 1, wherein said helix accommodating recess is provided by a step portion in said inner peripheral surface of said earseal.

6. An earcup assembly as claimed in claim 1, wherein said outer peripheral surface of said earseal includes a first portion adjacent said outer peripheral edge of said top that provides a first peripheral distance around said earseal, and a second portion adjacent said outer peripheral edge of said base that provides a second peripheral distance around said earseal, wherein said second peripheral distance is smaller than said first peripheral distance.

7. An earcup assembly as claimed in claim 6, wherein said first portion and said second portions of said outer peripheral surface define a step.

8. An earseal assembly as claimed in claim 1, wherein said earseal further includes a flexible sealed envelope defining said distal surface, as well as said inner and outer peripheral walls, said sealed envelope being adapted to contain a noise attenuating material.

9. An earseal for use in a headset and adapted to accommodate a helix of a user's ear, said earseal comprising:

an annular base providing a distal surface extending between inner and outer peripheral edges of said annular base, said distal surface being adapted for securing said earseal to the headset;

an annular top providing a proximal surface extending between inner and outer peripheral edges of said annular top, said proximal surface being adapted for contacting a user's head, and said proximal and distal surfaces being separated by a distance defining an earseal thickness;

an outer peripheral surface in communication with both said outer peripheral edge of said annular base and said outer peripheral edge of said annular top; and an inner peripheral surface in communication with both said inner peripheral edge of said annular base and said inner peripheral edge of said annular top, said inner peripheral surface providing a helix accommodating recess that is adapted to accommodate the helix of a user's ear, said helix accommodating recess defining a first portion of said inner peripheral surface adjacent said proximal surface and a second portion of said inner peripheral surface adjacent said distal surface, said first portion of said inner peripheral surface extending toward said distal surface a distance of at least about 20 percent of said earseal thickness.

10. An earcup assembly as claimed in claim 9, wherein said proximal surface has an area of less than about 9 square inches.

11. An earcup assembly as claimed in claim 9, wherein said earcup assembly provides attenuation of at least about 20 decibels for signals between about 1000 Hz and 2000 Hz.

12. An earcup assembly as claimed in claim 9, wherein said helix accommodating recess extends toward said outer peripheral surface of said earseal a distance of at least about 20 percent of the distance between said inner and outer peripheral edges of said annular top.

13. An earcup assembly as claimed in claim 9, wherein said helix accommodating recess is provided by a step portion in said inner peripheral surface of said earseal.

14. An earcup assembly as claimed in claim 9, wherein said outer peripheral surface of said earseal includes a first portion adjacent said outer peripheral edge of said top that provides a first peripheral distance around said earseal, and a second portion adjacent said outer peripheral edge of said base that provides a second peripheral distance around said earseal, wherein said second peripheral distance is smaller than said first peripheral distance.

15. An earcup assembly as claimed in claim 14, wherein said first portion and said second portions of said outer peripheral surface define a step.

16. An earseal assembly as claimed in claim 9, wherein said earseal further includes a flexible sealed envelope defining said distal surface, as well as said inner and outer peripheral walls, said sealed envelope being adapted to contain a noise attenuating material.

17. An earseal for use in a headset and adapted to accommodate a helix of a user's ear and to provide attenuation of at least about 30 decibels for signals between about 1000 Hz and 2000 Hz, said earseal comprising:

an annular base providing a distal surface extending between inner and outer peripheral edges of said annular base, said distal surface being adapted for securing said earseal to the headset;

an annular top providing a proximal surface extending between inner and outer peripheral edges of said annular top, said proximal surface being adapted for contacting a user's head, and said proximal and distal surfaces being separated by a distance defining an earseal thickness;

an outer peripheral surface in communication with both said outer peripheral edge of said annular base and said outer peripheral edge of said annular top; and an inner peripheral surface in communication with both said inner peripheral edge of said annular base and said inner peripheral edge of said annular top, said inner peripheral surface providing a helix accommodating recess that is adapted to accommodate the helix of a user's ear, said helix accommodating recess extending toward said outer peripheral surface of said earseal a distance of at least about 20 percent of the distance between said inner and outer peripheral edges of said annular top, and said helix accommodating recess defining a first portion of said inner peripheral surface adjacent said proximal surface and a second portion of said inner peripheral surface adjacent said distal surface, said first portion of said inner peripheral surface extending toward said distal surface a distance of at least about 20 percent of said earseal thickness.

* * * * *